United States Patent [19]

Mori

[11] Patent Number: 4,754,468
[45] Date of Patent: Jun. 28, 1988

[54] X-RAY COMPUTED TOMOGRAPHY SYSTEM

[75] Inventor: Issei Mori, Tochigi, Japan

[73] Assignee: Kabushiki Kaisha Toshiba, Kawasaki, Japan

[21] Appl. No.: 839,560

[22] Filed: Mar. 14, 1986

[30] Foreign Application Priority Data

Mar. 15, 1985 [JP] Japan .................................. 60-50331

[51] Int. Cl.$^4$ ............................................... A61B 6/00
[52] U.S. Cl. .......................................... 378/19; 378/4; 378/10
[58] Field of Search ....................... 378/4, 19, 10, 901, 378/99

[56] References Cited

U.S. PATENT DOCUMENTS

| | | |
|---|---|---|
| 3,432,657 | 3/1969 | Slavin . |
| 4,052,620 | 10/1977 | Brunnett et al. . |
| 4,063,792 | 12/1977 | Lodge . |
| 4,071,769 | 1/1978 | Brunnett et al. . |
| 4,135,247 | 1/1979 | Gordon et al. . |
| 4,149,247 | 4/1979 | Pavkovich et al. . |
| 4,158,142 | 6/1979 | Haimson . |
| 4,176,279 | 11/1979 | Schwierz et al. ........................ 378/4 |
| 4,181,939 | 1/1980 | Lyons . |
| 4,190,772 | 2/1980 | Dinwiddie et al. . |
| 4,211,925 | 7/1980 | Fairbairn . |
| 4,253,027 | 2/1981 | Taylor et al. . |
| 4,259,725 | 3/1981 | Andrews et al. . |
| 4,282,438 | 8/1981 | Nishida et al. . |
| 4,284,896 | 8/1981 | Stonestrom ........................ 364/414 |
| 4,309,615 | 1/1982 | Kowalski . |
| 4,352,021 | 9/1982 | Boyd et al. . |
| 4,365,339 | 12/1982 | Pavkovich et al. . |
| 4,394,737 | 7/1983 | Komaki et al. . |
| 4,426,715 | 1/1984 | Baer et al. . |
| 4,455,667 | 6/1984 | Schwierz et al. . |
| 4,477,922 | 10/1984 | Liebetruth . |

Primary Examiner—Janice A. Howell
Assistant Examiner—David P. Porta
Attorney, Agent, or Firm—Finnegan, Henderson, Farabow, Garrett & Dunner

[57] ABSTRACT

An X-ray CT system includes an X-ray source, a drive device, an X-ray detector, a data acquisition system, a reconstruction processor and a delay circuit. The X-ray source emits an X-ray fan beam onto an object and is rotated by the drive device on substantially the same plane as the fan beam. A graticule sensor detects an angular position of the X-ray source. The X-ray detector consists of detector elements fixed concentrically with a relative rotational path of the X-ray source. The data acquisition system responds to a position signal from the graticule sensor and samples the output data from the detector for each predetermined angular position of the X-ray source to obtain projection data. The projection data is reconstructed by the reconstruction processor to obtain a tomographic image of the object. The delay circuit delays the position signal from the graticule sensor to offset the sampling point of the projection data by a ¼ sampling point pitch from the angle corresponding to the center of each detection element.

3 Claims, 6 Drawing Sheets

#N of N detector elements of detector 3, some
X-RAY COMPUTED TOMOGRAPHY SYSTEM

BACKGROUND OF THE INVENTION

The present invention relates to an X-ray Computed Tomography system which has an X-ray source for generating an X-ray fan beam and a multiple element ring detector, X-ray detector elements of which are arranged in a ring-like shape, wherein an X-ray beam is emitted to an object to be examined located substantially at the center of the ring detector while the X-ray source is rotated substantially concentrically with the ring detector, and a tomographic image of the object is reconstructed using projection data from the ring detector portion located opposite the X-ray source with the object interposed therebetween.

Figure 1:
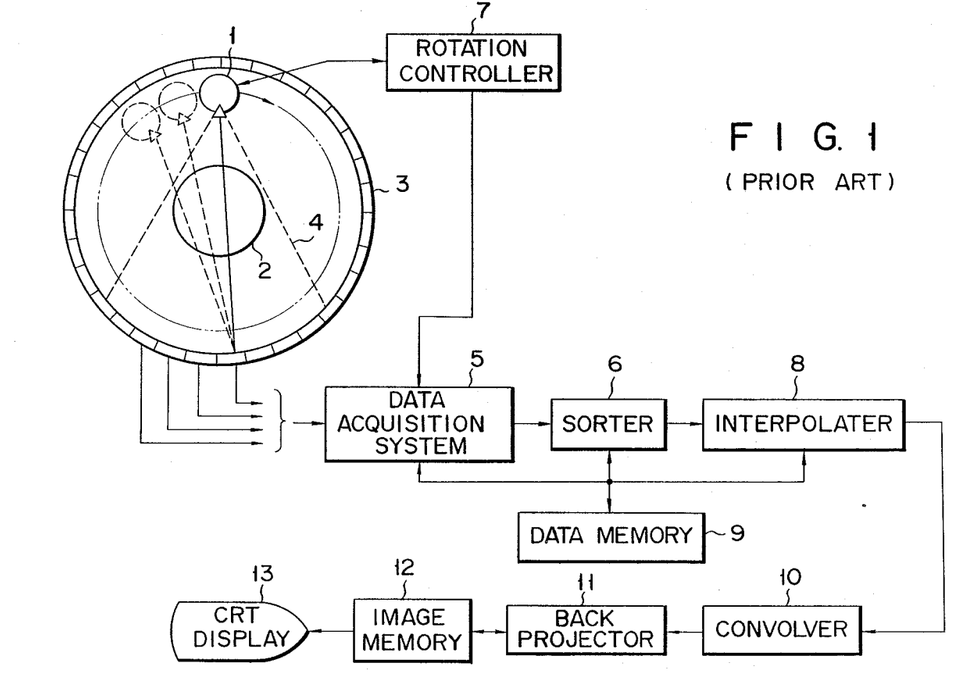
FIG. 1 is a block diagram schematically showing an arrangement of a conventional X-ray CT system.

A conventional X-ray CT system of this type is schematically shown in FIG. 1. The system includes X-ray source 1, ring detector 3, data acquisition system (DAS) 5, sorter 6, rotation controller 7, interpolater 8, data memory 9, convolver 10, back projector 11, image memory 12 and cathrode ray tube (CRT) display 13. Source 1, constituted by an X-ray tube, is driven and controlled by controller 7. Source 1 emits X-ray fan beam 4, toward object 2 while being rotated thereabout. Ring detector 3, concentric with the rotational center of source 1, is fixed outside the rotating path of source 1. Detector 3 is comprised of a large number of X-ray detector elements arranged to form a ring. Beam 4 transmitted through object 2, is incident on the detector elements of detector 3 which are opposite source 1 with object 2 interposed therebetween. X-rays incident on these detector elements are converted to an electrical signal having a magnitude corresponding to the light intensity. This electrical signal is then supplied to DAS 5.

A cylindrical graticule (not shown) is fixedly disposed concentric with detector 3. The graticule has transparent and opaque portions alternately arranged at angular intervals on a circle. The number of transparent or opaque portions thereof is twice the number of the detector elements in detector 3. The transparent or opaque portions of the graticule are detected by a photointerrupter (not shown) moved along the circle in synchronism with source 1. Light detected by the photointerrupter is converted to electrical pulses generated at a pitch half that of the array of the detector elements upon rotation of source 1. The detection system consisting of the graticule and photointerrupter is hereinafter referred to as a graticule sensor.

Electrical pulses from the graticule sensor are then supplied to controller 7. Controller 7 controls the rotation of source 1 in response to the pulses from the graticule sensor. These pulses are also supplied to DAS 5.

DAS 5 samples electrical signals from detector 3 in response to pulses from the graticule sensor, i.e., in response to the rotation of source 1, and converts them into digital signals. Digital signals from DAS 5 are then supplied to sorter 6. For each sampling, i.e., each projection, projection data is supplied to sorter 6 and serves as projection data (hereinafter referred to as source fan data) corresponding to X-ray paths (hereinafter referred to as a source fan) projected in a fan shape with source 1 at its center. Sorter 6 rearranges source fan data obtained by a plurality of successive projections to data (hereinafter referred to as a detector fan data) corresponding to the source fan (hereinafter referred to as a detector fan) expanded from each detector element.

The detector fan data (hereinafter referred to as first detector fan data) from sorter 6 is then supplied to interpolater 8. Interpolater 8 interpolates the first detector fan data corresponding to the X-ray paths passing the positions (at equal angular intervals with respect to the center of rotation of source 1) of source 1 and the detector elements. Interpolater 8 then calculates second detector fan data corresponding to predetermined X-ray paths which are arranged at equal angular intervals as viewed from the respective detector elements. Memory 9 is connected to DAS 5, sorter 6 and interpolater 8 to help the respective processing thereof. The second detector fan data from interpolater 8 is supplied to convolver 10. Convolver 10 performs convolution as a kind of filtering of the second detector fan data so as to prevent an image from being blurred upon back projection thereof, thereby obtaining third detector fan data. The third detector fan data from convolver 10 is supplied to back projector 11. Projector 11 projects the third detector fan data back to memory 12, which stores a memory space corresponding to coordinates of a slice of object 2. Back projection by projector 11 is performed such that sequential third detector fan data is accumulated and written in correspondence with the X-ray path position. The third detector fan data accumulated in memory 12 therefore allows reconstruction of image data representing a slice of object 2. The reconstructed image is then read out from memory 12 and displayed on display 13.

The positional relationship between each detector element of detector 3 and the sampling point (the position of source 1 at the time of sampling) of DAS 5 in the conventional X-ray CT system will be described with reference to FIG. 2.

Figure 2:
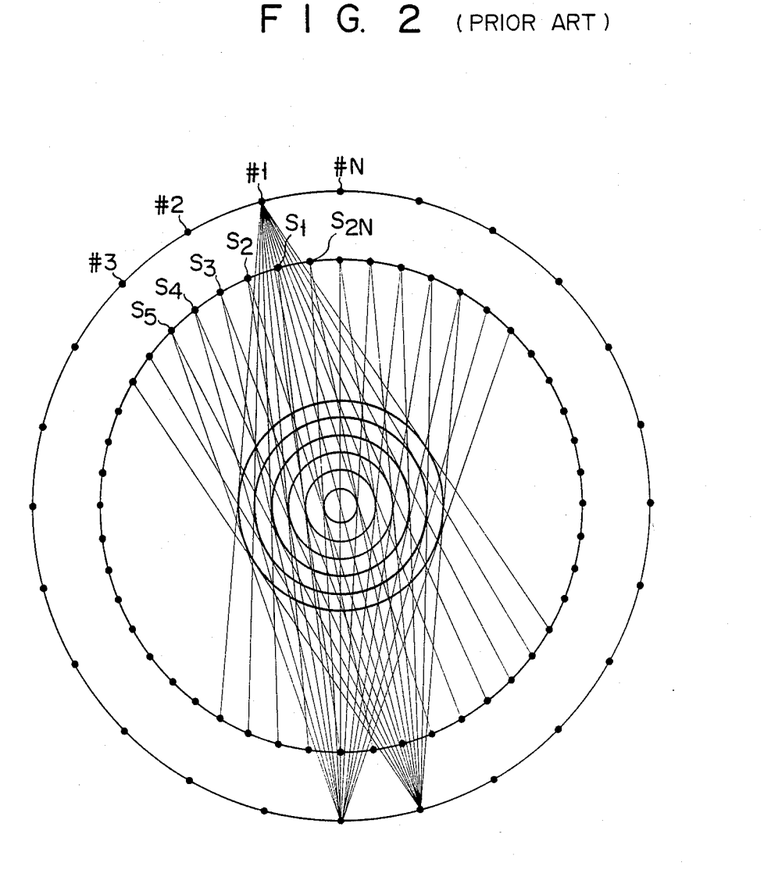
FIG. 2 is a representation showing the relationship between the X-ray detector elements and the sampling points in the system of FIG. 1.

As shown in FIG. 2 for each of central points #1, #2, . . . #N of N detector elements of detector 3, some sampling points correspond to each other (located at the same angle with respect to the center of rotation of source 1) among 2N sampling points $S_1, S_2, \ldots S_{2N}$ of DAS 5 (in this case, some sampling points do not correspond to each other).

When detector fan data is obtained, the sampling pitch depends on the pitch between points $S_1, S_2, \ldots S_{2N}$. Thus, the highest possible resolution is determined by this pitch.

U.S. Pat. No. 4,176,279 describes an X-ray CT system of a type (so-called third generation type) wherein an X-ray source for generating an X-ray fan beam and a detector for detecting the beam are arranged opposite each other in relation to the object to be examined, and the X-ray source and the detector are rotated together around the object. According to a known technique for improving image quality of the reconstructed image, the detector is offset by a ¼ pitch of the detector elements, and the pitch of the projection data (X-ray path) to be sampled can be doubled.

However, in a CT system of the type shown in FIGS. 1 and 2, fixed detector 3 cannot be offset by a ¼ pitch of the detector elements.

SUMMARY OF THE INVENTION

It is an object of the present invention to provide an X-ray CT system wherein a pitch of projection data (X-ray paths) to be sampled can be decreased to about ½ even in a fixed ring detector system.

Additional objects and advantages of the invention will be set forth in part in the description which follows, and in part will be obvious from the description, or may be learned by practice of the invention. The objects and advantages of the invention may be realized and attained by means of the instrumentalities and combinations particularly pointed out in the appended claims.

In order to achieve the above objects of the present invention, there is provided an X-ray CT system comprising: an X-ray source for generating an X-ray fan beam; a drive device for causing relative rotation between the X-ray source and the object, the X-ray source being rotated about the object in the same plane as a fan-shaped beam while emitting the X-ray fan beam onto the object, the drive device being adapted to generate a position signal representing a relative rotational position; an X-ray detector including a plurality of detector elements which are concentric with a rotational path of the X-ray source, are arranged at equal angular intervals, and have a fixed position relative to the object, the X-ray detector being adapted to generate projection data corresponding to an amount of the X-ray beam transmitted through the object in units of detector elements; a data acquisition system, responsive to the position signal from the drive device, for sampling output data from the detector for each predetermined angle of the relative rotation of the X-ray source and acquiring projection data; a reconstruction processing section for reconstructing the projection data acquired by the data acquisition system to form a tomographic image of the object; and an offset system, arranged in association with at least one of the drive device and the data acquisition system, for offsetting sampling points of the projection data by ¼ of the sampling point pitch from a point corresponding to the center of each detector element.

According to the present invention, even in an X-ray CT system with a fixed X-ray multiple detector element ring detector, a sampling density, i.e., a density of projection data used for image reconstruction can be increased. Therefore, a tomographic image free from an aliasing-originated artifact, i.e., an artifact caused by a coarse sampling density, can be reconstructed. Furthermore, the spatial resolution of the reconstructed tomographic image can be increased due to the improvement of the sampling density.

DETAILED DESCRIPTION OF THE PREFERRED EMBODIMENT

An X-ray CT system according to an embodiment of the present invention will be described with reference to FIG. 3.

Figure 3:
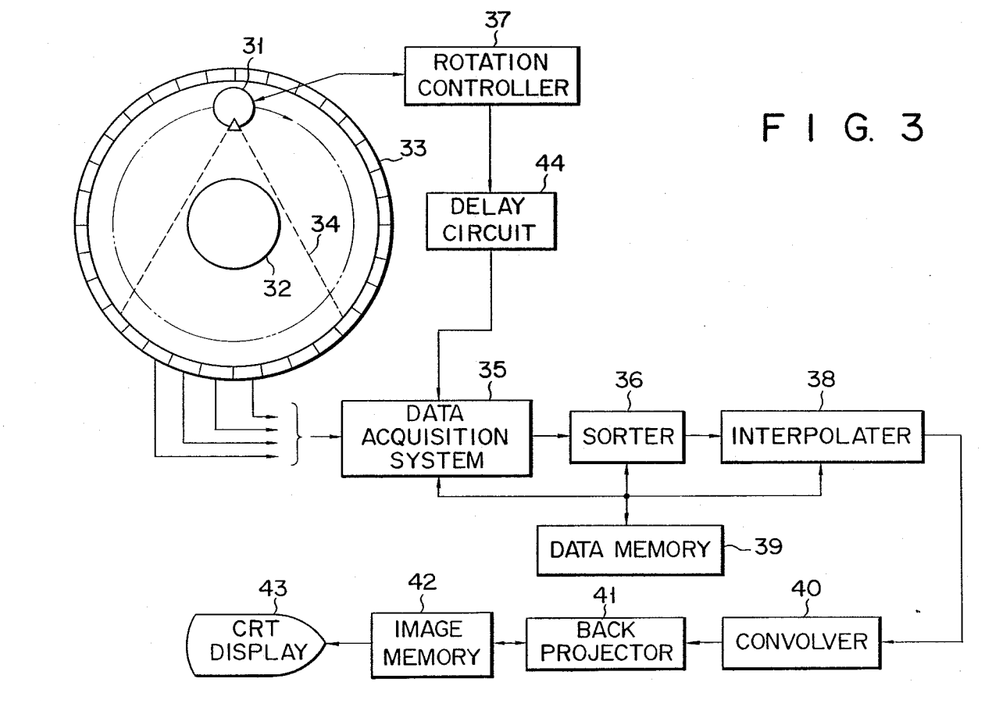
FIG. 3 is a block diagram schematically showing an arrangement of an X-ray CT system according to an embodiment of the present invention.

The X-ray CT system in FIG. 3 includes X-ray source 31, ring detector 33, DAS 35, sorter 36, rotation controller 37, interpolater 38, data memory 39, convolver 40, back projector 41, image memory 42, CRT display 43 and delay circuit 44. Source 31, detector 33, DAS 35, sorter 36, controller 37, interpolator 38, memory 39, convolver 40, projector 41, memory 42 and display 43 have substantially the same functions as those of source 1, detector 3, DAS 5, sorter 6, controller 7, interpolator 8, memory 9, convolver 10, projector 11, memory 12 and display 13 of FIG. 1, respectively.

Source 31 is driven and controlled by controller 37. Source 31 rotates about object 32 while emitting X-ray fan beam 34. Detector 33 concentric with the rotational center of source 31 is fixed outside the path of source 31. Detector 33 is comprised of a large number of X-ray detector elements arranged to form a ring. Beam 34 transmitted through object 32 is incident on the detector elements of detector 33 which are opposite source 31. The X-ray incident on these detector elements is converted to an electrical signal, the magnitude of which corresponds to the intensity of the incident X-rays. The electrical signal is supplied to DAS 35.

A cylindrical graticule (not shown) is fixedly disposed concentric with detector 33. The graticule has transparent and opaque portions alternately on a circle. The number of transparent or opaque portions is twice the number of the detector elements in detector 33. The transparent or opaque portions of the graticule are detected by a photointerrupter (not shown) moved along the circle in synchronism with source 31. A detection signal from detector 33 is converted to electrical pulses generated at a pitch half that of the array of the detector elements upon rotation of source 31. The graticule and the photointerrupter constitute a graticule sensor. Alternatively, a graticule can be rotated in synchronism with source 31, and a photointerrupter can be fixed together with detector 33 to constitute a graticule sensor. Furthermore, the graticule sensor may be constituted by a graticule with alternate reflecting and nonreflecting portions and a photosensor for detecting reflection/nonreflection of the graticule.

Electrical pulses from the graticule sensor are supplied to controller 37. Controller 37 controls the rotation of source 31 in response to the pulses from the graticule sensor, and at the same time outputs these pulses.

The detection pulses of the graticule sensor are supplied from controller 37 to delay circuit 44. Circuit 44 delays the pulses from the graticule sensor by a ¼ sampling pitch from the center of the detector element. A delayed signal is supplied to DAS 35. In synchronism with delayed pulses from circuit 44, DAS 35 samples electrical signals from detector 33. The data sampled by the delayed pulses are processed in the same manner as the conventional system.

The data is sampled and converted by DAS 35 to a digital signal. The digital signal is supplied to sorter 36. For each sampling or projection, the projection data is supplied to sorter 36 and serves as source fan data corresponding to the fan-shaped X-ray paths with source 31 as the center. Sorter 36 rearranges the source fan data obtained by successive projection operations to obtain first detector fan data corresponding to the fan-shaped X-ray paths expanded from each detector element. The first detector fan data from sorter 36 is supplied to interpolator 38. Interpolator 38 interpolates the first detector fan data corresponding to the X-ray paths passing the positions of source 31 and the detector elements and generates second detector fan data corresponding to predetermined X-ray paths at equal angular intervals as viewed from the respective detector elements. Memory 39 connected to DAS 35, sorter 36 and interpolator 38 helps the respective processing thereof. The second detector fan data from interpolator 38 is supplied to convolver 40. Convolver 40 performs convolution of the second detector fan data so as to prevent an image from being blurred upon back projection thereof, thereby obtaining third detector fan data. The third detector fan data from convolver 40 is supplied to back projector 41. Projector 41 projects the third detector fan data back to memory 42 with a memory space corresponding to coordinates of a slice of object 32. Back projection by projector 41 is performed such that the third detector fan data is accumulated and written in correspondence with the X-ray path position. The third detector fan data is then accumulated in memory 42, thereby reconstructing image data representing a slice of object 32. The reconstructed image is then read out from memory 42 and displayed on display 43.

Figure 4:
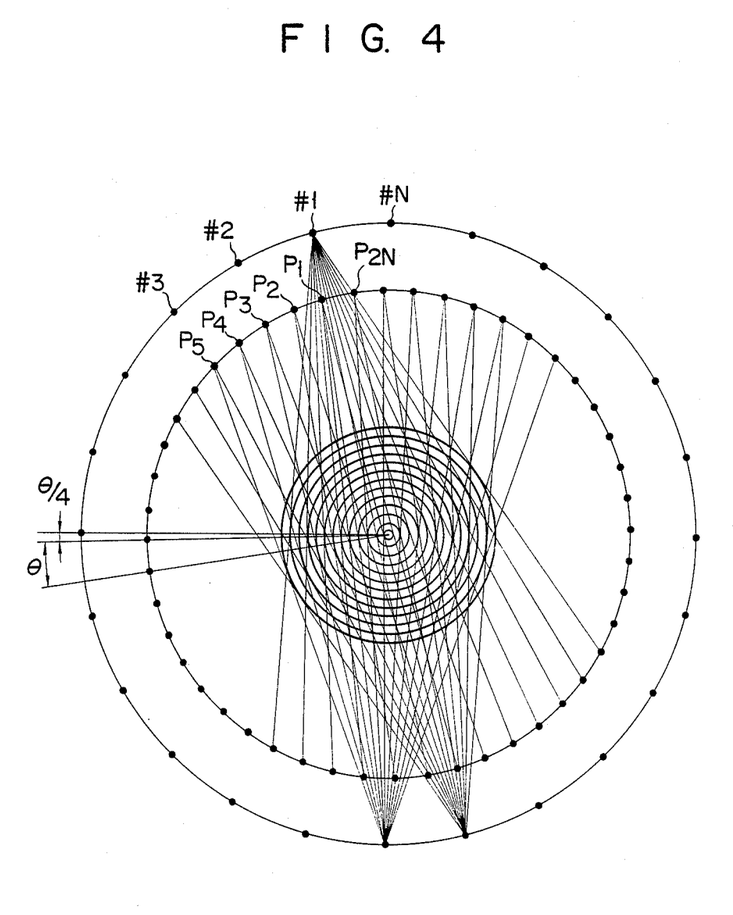
FIG. 4 is a representation showing the relationship between the X-ray detector elements and the sampling points in the system of FIG. 3.

The positional relationship between each detector element of detector 33 in the present invention and the sampling point of DAS 35 will be described with reference to FIG. 4.

Sampling points $P_1, P_2, \ldots P_{2N}$ of DAS 35 are offset by $\frac{1}{4}$ angular pitch $\theta$ from central points #1, #2, ... #N of the detector elements of detector 33. X-ray paths corresponding to detector fan data opposing each other at an angle of 180 degrees with respect to the rotational center are offset by $\frac{1}{2}$ the angular pitch of the sampling points.

Pitches of concentric circles contacting the X-ray paths are doubled as compared with the conventional example of FIG. 2. In other words, the sampling density is doubled as compared with the conventional system.

The present invention is not limited to the embodiment described above.

Figure 5:
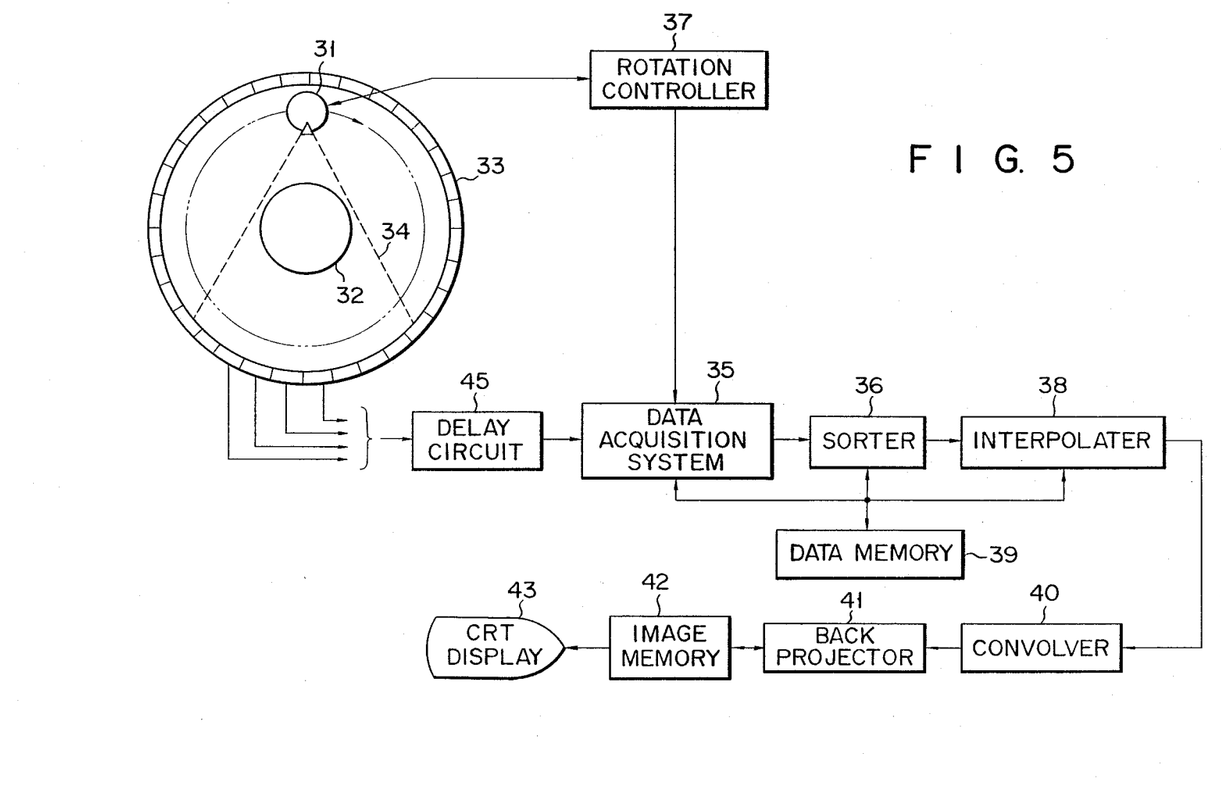
FIG. 5 is a block diagram schematically showing an arrangement of an X-ray CT system according to another embodiment of the present invention.

For example, as shown in FIG. 5, delay circuit 45 can be arranged between detector 33 and DAS 35, instead of arranging circuit 44 between controller 37 and DAS 35.

Alternatively, in place of circuit 44, a positional offset corresponding to a $\frac{1}{4}$ sampling pitch can be provided between source 31 and the graticule sensor.

Furthermore, the density of the graticule can be increased four times, thus, the graticule sensor of controller 37 can output a pulse at every $\frac{1}{4}$ sampling pitch, and sampling for every 4 pitches can be performed from a position offset by one pitch of the graticule from the position of each detector element in detector 33.

Figure 6:
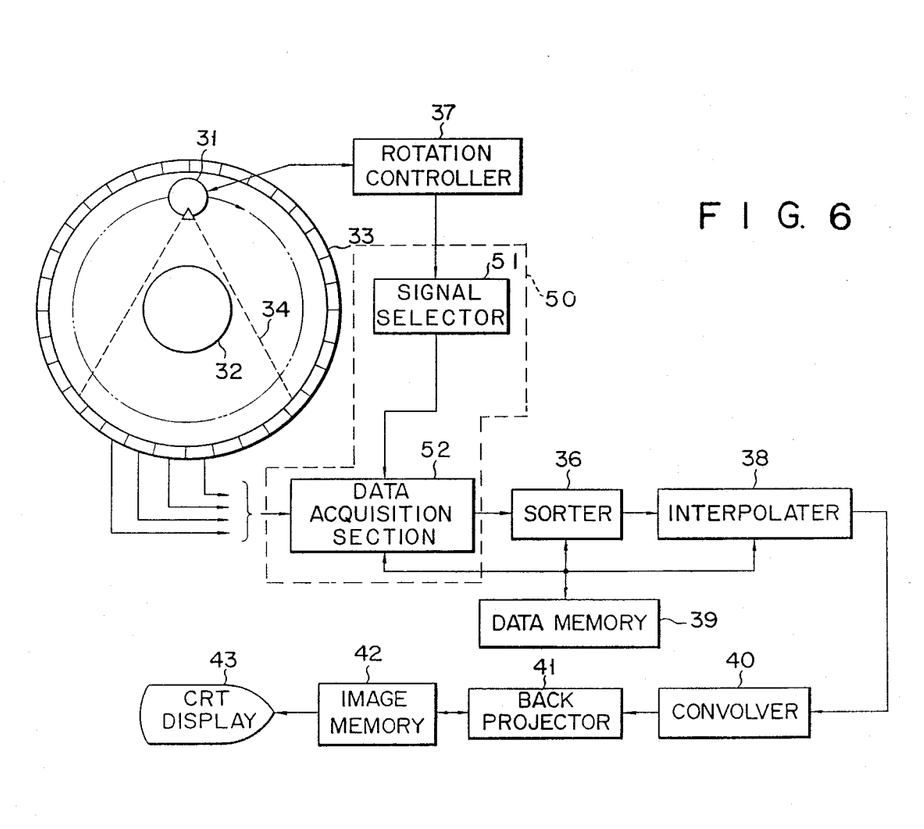
FIG. 6 is a block diagram schematically showing an arrangement of an X-ray CT system according to a third embodiment of the present invention.

More specifically, as shown in FIG. 6, data acquisition system 50 has signal selector 51 and data acquisition section 52. Signal selector 51 selects every fourth pulse, each pulse being offset by $\frac{1}{4}$ sampling pitch from the position of each detector element of detector 33, from among the pulses output by the graticule sensor of rotation controller 37 at $\frac{1}{4}$ sampling pitch. The pulse selected by signal selector 51 is supplied to data acquisition section 52. Section 52 performs data acquisition similar to that carried out by data acquisition system 35 shown in FIG. 3.

As in U.S. Pat. No. 4,284,896, data components between adjacent X-ray paths of the detector fan data for a given detector element can be interpolated using the detector fan data from detector elements facing the given detector element. Detector fan data including the interpolated data can then be convoluted and back-projected. The spatial resolution of the tomographic image can be greatly improved, in this case.

What is claimed is:

1. An X-ray CT system comprising:
   an X-ray source for generating an X-ray fan beam;
   driving means for rotating said X-ray fan beam relative to an object to be examined in a plane in which said X-ray fan beam exists, said driving means generating a position signal representing a relative rotational position;
   stationary X-ray detecting means including a plurality of detector elements which are concentric with a rotational orbit of said X-ray source, a plurality of detection points of said detector elements being arranged at equal angular intervals, said stationary X-ray detecting means generating projection data for each of said detection points corresponding to an internsity of the X-ray beam transmitted through the object and impinged on said detector elements for each of said detection points;
   data acquisition means, responsive to the position signal from said driving means, for sampling said projection data from said X-ray detecting means at co-angular sampling points relative to the rotation of said X-ray beam;
   reconstruction processing means for reconstructing the projection data acquired by said data acquisition means to form a tomographic image of the object; and
   offset means, arranged in association with at least one of said driving means and said data acquisition means, for offsetting said sampling points of the projection data by $\frac{1}{4}$ of a distance of the adjacent sampling points relative to said detection points, said offset means including
   position detecting means, arranged in said driving means, for detecting a position of the relative rotation and outputting the position signal, and
   delaying means, arranged between said position detecting means and said data acquisition means, for delaying the position signal to offset said sampling points of the projection data by $\frac{1}{4}$ of the distance of the adjacent sampling points relative to said detection points.

2. An X-ray CT system comprising:
   an X-ray source for generating an X-ray fan beam;
   driving means for rotating said X-ray fan beam relative to an object to be examined in a plane in which said X-ray fan beam exists, said driving means generating a position signal representing a relative rotational position;
   stationary X-ray detecting means including a plurality of detector elements which are concentric with a rotational orbit of said X-ray source, a plurality of detection points of said detector elements being arranged at equal angular intervals, said stationary X-ray detection means generating projection data for each of said detection points corresponding to an intensity of the X-ray beam transmitted through the object and impinged on said detector elements for each of said detection points;

data acquisition means, responsive to the position signal from said driving means, for sampling said projection data from said X-ray detecting means at co-angular sampling points relative to the rotation of said X-ray beam;

reconstruction processing means for reconstructing the projection data acquired by said data acquisition means to form a tomographic image of the object; and offset means, arranged in association with at least one of said drving means and said data acquisition means, for offsetting said sampling points of the projection data by ¼ of a distance of the adjacent sampling points relative to said detection points, said offset including position detecting means, arranged in said driving means, for outputting 4 different position signals shifted by a ¼ pitch of said sampling points with respect to the rotation of said X-ray fan beam, and signal selecting means, for selecting one of said 4 different signals which is offset by ¼ of said distance of the adjacent samplng points relative to said detection points and for supplying the selected position signal to said data acquisition means.

3. An X-ray CT system comprising:

an X-ray source for generating an X-ray fan beam;

driving means for rotating said X-ray fan beam relative to an object to be examined in a plane in which said X-ray fan beam exists, said driving means having a signal generating means for generating a position signal representing a relative rotational position;

stationary X-ray detecting means including a plurality of detector elements which are concentric with a rotational orbit of said X-ray source, a plurailty of detection points of said detector elements being arranged at equal angular intervals, said stationary X-ray detecting means generating projection data for each of said detection points corresponding to an intensity of the X-ray beam transmitted through the object and impinged on said detector elements for each of said detection points;

data acquisition means, responsive to the position signal from said driving means, for sampling said projection data from said X-ray detecting means at co-angular sampling points relative to the rotation of said X-ray beam; and reconstruction processing means for reconstructing the projection data acquired by said data acquisition means to form a tomographic image of the object, said signal generating means generating the position signal according to said sampling points of the projection data offset by ¼ of a distance of the adjacent sampling points relative to said detection points.

* * * * *